United States Patent [19]
King et al.

[11] Patent Number: 5,522,897
[45] Date of Patent: Jun. 4, 1996

[54] DISPOSABLE PROVISIONAL INSTRUMENT COMPONENT FOR EVALUATING THE FIT OF AN ORTHOPAEDIC IMPLANT

[75] Inventors: Richard S. King; Thirumalai N. C. Devanathan, both of Warsaw; Steve T. Lin, Fort Wayne; William L. Rohr; Dale F. Swarts, both of Warsaw, all of Ind.

[73] Assignee: Zimmer, Inc., Warsaw, Ind.

[21] Appl. No.: 422,193

[22] Filed: Apr. 13, 1995

Related U.S. Application Data

[62] Division of Ser. No. 233,864, Apr. 20, 1994, Pat. No. 5,472,415.

[51] Int. Cl.$^6$ ................................ A61F 2/28; A61F 5/00
[52] U.S. Cl. ........................... 623/16; 623/11; 606/102; 604/110; 604/111
[58] Field of Search ..................... 623/11, 16, 18; 604/110, 111, 199; 606/102; 524/88

[56] References Cited

U.S. PATENT DOCUMENTS

| | | | |
|---|---|---|---|
| 3,874,383 | 4/1975 | Glowacki | 604/199 |
| 4,135,517 | 1/1979 | Reale | 128/303 R |
| 4,281,420 | 8/1981 | Raab | 3/1.912 |
| 4,336,618 | 6/1982 | Raab | 3/1.913 |
| 4,341,691 | 7/1982 | Anuta | 523/116 |
| 4,491,987 | 1/1985 | Park | 3/1.91 |
| 4,801,295 | 1/1989 | Spencer | 604/198 |
| 4,820,755 | 4/1989 | Webster | 524/88 |
| 5,098,437 | 3/1992 | Kashuba et al. | 606/89 |
| 5,156,626 | 10/1992 | Broderick et al. | 623/22 |
| 5,171,243 | 12/1992 | Kashuba et al. | 606/86 |
| 5,263,991 | 11/1993 | Wiley et al. | 623/66 |

OTHER PUBLICATIONS

Biomet, Inc. –"Bio –Moore Modular Endoprosthesis System "–August 1985.
Biomet, Inc. –"Bi–Polar Articulating Hip System "–No date available.
Howmedica –"Centrax Bipolar System"–1987.
Orthopaedic Device Corporation –Endo Head–Neck Extension–No date available.
3M –Bateman UPF Universal Proximal Femur –No date available.
Zimmer, Inc. –Zimmer Endoprostheses –Lit. No. 83–001–4005–0242–1983.
Zimmer, Inc. –Universal Acetabular Provisionals –1988.
Zimmer, Inc. Bi –Articular II Hip Provisionals –1988.
Zimmer, Inc. –"Precoat Plus Distal Centralizer"–2/24/89.
Zimmer, Inc. –"Cleaning and Sterilizing Instructions for Implant Components and Provisionals "–87–6203–066–00, 1991.
Zimmer, Inc. –"Care, Maintenance and Sterilization of Zimmer Orthopaedic Manual Instruments"–Lit No. 97–5000–170 –1988.
AORN Congress publication –"Sterilization of Medical Devices "–M. Reichert–1987.

*Primary Examiner*—Randy C. Shay
*Attorney, Agent, or Firm*—Margaret L. Geringer

[57] ABSTRACT

A provisional instrument component 1 for evaluating the fit of a corresponding orthopaedic implant. The component 1 is intended and designed to be a disposable, single use provisional instrument component. The provisional instrument component 1 is made of a material which can be sterilized by gamma irradiation, but which provides a visible indicator, such as visible deformation 10, upon resterilization by exposure to a heated environment, thereby discouraging or preventing re-use of the component 1.

14 Claims, 2 Drawing Sheets

DISPOSABLE PROVISIONAL INSTRUMENT COMPONENT FOR EVALUATING THE FIT OF AN ORTHOPAEDIC IMPLANT

This is a division of application Ser. No 08/233,864 filed Apr. 20, 1994 now U.S. Pat. No. 5,472,415.

FIELD OF THE INVENTION

The invention relates to the field of provisional instrument componet which are used for evaluating the fit of a corresponding orthopaedic implant. In particular, this invention relates to such provisional components which are disposable or designed for single use.

BACKGROUND OF THE INVENTION

Typically, provisional components are designed to be reused, and have been known to be made out of various sturdy, reusable materials, such as stainless steel, cobalt chromium-molybdenum alloy, titanium or titanium alloy, aluminum (including anodized or Teflon coated aluminum), Delrin polyacetal, Celcon polyacetal copolymer, Ultraform polyacetal copolymer, polysulfone, and Ultem polyetherimide, as well as possible other similar reusable materials.

Although provisional components are not implanted, they must still be sterilized for surgical use since provisional components are used in surgery. Although provisional components could initially be provided presterilized, they are usually supplied nonsterile. If provided nonsterile, they must be sterilized before they are used. In addition, all provisional components must be resterilized before each additional surgical use. Typically, nonsterile provisional components are steam sterilized in an autoclave. Polyformaldehyde resins, such as polyacetals or polyacetal copolymers, have a somewhat limited life expectancy when subjected to repeated steam sterilization. However, polyacetal parts have been shown to withstand approximately 50 autoclaving or steam sterilization cycles. It is recommended that when the surface of such items becomes chalky, the item should be replaced.

There are three main types of sterilization procedures: gamma irradiation; steam sterilization; and ethylene oxide (EO) sterilization.

Gamma irradiation is used to produce a sterile product by exposing a product to radiation emitted by radioactive decay, and as such, is only available from a limited number of vendors that provide this process. Thus, this process is a commercially available process, and is not available in health care facilities, such as hospitals. This process can be applied to products through certain types of packaging materials, and as such, is an effective way of providing presterilized packaged products to the customer. Heat or high temperatures are not generated with this procedure.

Steam sterilization is used to produce a sterile product by direct contact of all surfaces of the device or instrument with steam and then revaporization of the water condensate to produce a sterile, dry product. The steam is produced by heating water above its boiling point. When steam contacts the device or instrument, a water condensate is left on the device. A drying phase is utilized to revaporize the condensate and dry the device or instrument. The vapor is removed from the steam sterilizer during this drying phase.

There are different methods of steam sterilization, such as gravity displacement and high vacuum, prevacuum, or pulsating vacuum. These steam sterilization procedures are typically conducted at temperatures of about 250° to 270° F. in a chamber often referred to as an autoclave. It is noted that sometimes a variation of the steam sterilization procedure is utilized by using a gravity displacement sterilizer when there is insufficient time to sterilize by the preferred wrapped or container method. This is sometimes referred to as "flash" sterilization, and is not typically a preferred method, except as an emergency procedure. Steam sterilizers or autoclaves are typically available in health care facilities, such as hospitals.

Ethylene oxide (EO) sterilization is used to produce a sterile product by exposing a product to ethylene oxide gas. This procedure is typically carried out at lower temperatures than steam sterilization. For example, the temperature of the sterilization phase for EO sterilization is generally 120° to 145° F. for a warm cycle or 85° to 100° F. for a cold cycle. However, the lower the temperature at which an item is sterilized, the longer it must be submitted to EO gas. EO sterilization is typically used for products which will not tolerate the high temperatures and/or moisture associated with steam sterilization. EO sterilization produces toxic residuals which dissipate upon adequate aeration. Thus, when using EO sterilization, an appropriate and effective exposure time to the EO gas and appropriate aeration time must be determined. Many medical materials and/or devices have not had appropriate tests for EO residue levels or sterility validation conducted on them. Such tests must be conducted before EO sterilization can be recommended for use on new, previously untested materials. It is noted that very few studies have been done on a potential buildup of EO residuals on repeated sterilization. Thus, repeated sterilization on a given product, more typically utilizes steam sterilization. Typically, polyethylene-containing implants are EO sterilized because the temperatures of steam sterilization can adversely affect the polyethylene components' dimensional stability. However, implants are not typically repeatedly sterilized. EO sterilizers are also typically available at health care facilities, such as hospitals.

It is noted that metal implants having a thin poly methyl methacrylate (PMMA) coating (such as disclosed in U.S. Pat. Nos. 4,491,987; 4,336,618; and 4,281,420) can be steam sterilized, which slightly softens the coating. However, the metal base of the implant enables the device to maintain the integrity of its shape and structure. Such PMMA coated implants could also be EO sterilized.

In addition, it is known to provide single use implants, such as distal centralizers (which are used to center the distal tip of a femoral hip stem) made from polymethyl methacrylate. These implants are not to be resterilized by steam sterilization, as such resterilization could destroy the structural integrity of the implant; however, they may be resterilized by ethylene oxide.

SUMMARY OF THE INVENTION

The present invention provides a provisional instrument component for evaluating the fit of a corresponding orthopaedic implant. The component is intended and designed to be a disposable, single use provisional instrument component. The provisional instrument component is made of a material or combination of materials which can be initially commercially sterilized by gamma irradiation, but which provides a visible indicator upon resterilization by exposure to a heated environment to discourage or prevent reuse of the component. The visible indicator may be visible deformation upon resterilization by exposure to the heated environment, or other suitable visible indicator.

Accordingly, it is an advantage of the invention to provide a novel, disposable, single use provisional instrument component.

Another advantage of the invention is that the provisional component provides a visible indicator upon resterilization by exposure to a heated environment to prevent reuse, which is advantageous because prevention of reuse lessens the risk of transmission of infectious diseases, such as AIDS or hepatitis, which is a risk if resterilization is not done properly.

A further advantage of the invention is that in a preferred embodiment of the invention, the provisional component will visibly deform upon resterilization in a steam sterilizer or autoclave.

A still further advantage of the invention is to provide such a provisional component which is economical and simple to manufacture, and yet has the additional benefit of helping to prevent reuse of the component by providing a visible indicator upon exposure to a heated environment, especially such heat as is generated by a steam sterilizer.

Another advantage of the invention is to provide such a provisional component which thus ensures the accuracy of the single use provisional component.

Still other advantages of the invention will become apparent upon reference to the accompanying drawings.

DESCRIPTION OF THE PREFERRED EMBODIMENT

The preferred embodiment described herein is not intended to be exhaustive or to limit the invention to the precise form disclosed. Rather it is chosen and described to best explain the invention, so that others skilled in the art might utilize its teachings.

Figure 1:
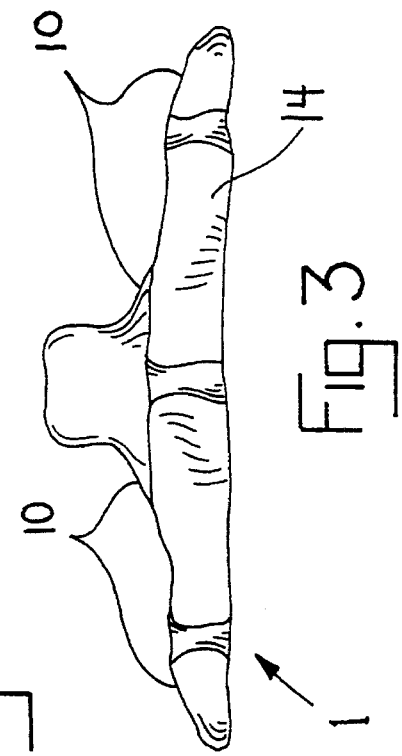
FIG. 1 is a perspective view of a representative provisional instrument component in accordance with the present invention.
Figure 2:
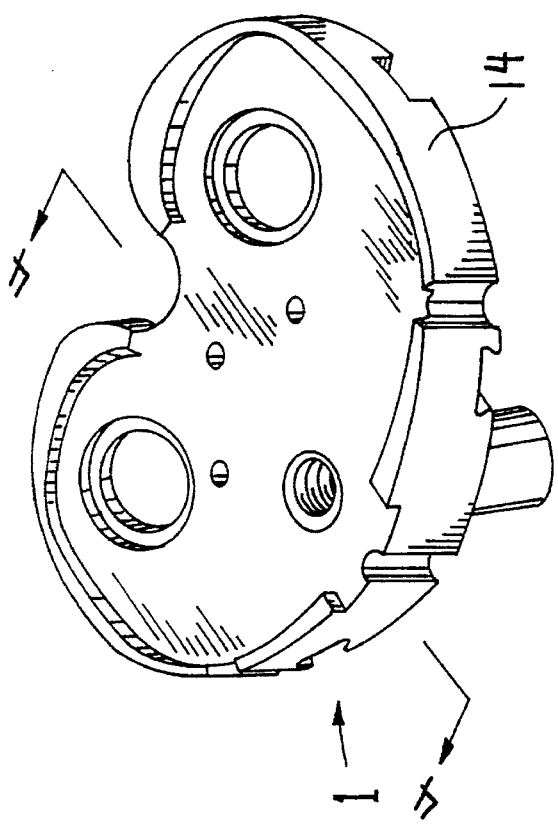
FIG. 2 is a front view of the component of FIG. 1.

Accordingly, FIGS. 1 and 2 illustrate a representative provisional instrument component 1. The component 1 illustrated is a tibial plate provisional component (which is typically used in conjunction with a tibial articulating surface provisional component, not shown) for evaluating the fit of a corresponding knee implant prosthesis. However, it is understood that the principles of the present invention can be applied to any suitable type or configuration for a provisional instrument component, including but not limited to, tibial provisionals, femoral knee provisionals, femoral head provisionals, femoral hip stem provisionals, fracture fixation provisionals, or any other suitable provisional component.

In general, a provisional component 1 is not used in static or dynamic loading environments, since they are primarily used for evaluating the fit of a corresponding orthopaedic implant. They enable the surgeon to confirm proper fit and to make any necessary adjustments to the fit before implanting the actual corresponding orthopaedic implant device. Therefore, the provisional component 1 is utilized as instrumentation, and will not remain implanted or in the body. Thus, performance requirements are less stringent than those needed for the corresponding implant device.

Cost is becoming increasingly important in today's competitive medical device market. Material selection and processing technique are major factors in the determination of a medical device's cost and performance. As noted above, provisional components, such as 1, are not used in static or dynamic loading environments, and performance requirements are less stringent than those required for the corresponding implant device. Thus, a disposable provisional component manufactured from a lower cost material which is intended and designed to be a disposable, single use provisional instrument component is a viable alternative to the reusable provisional components which are made of sturdier materials and are able to withstand multiple uses and multiple resterilizations.

Figure 3:
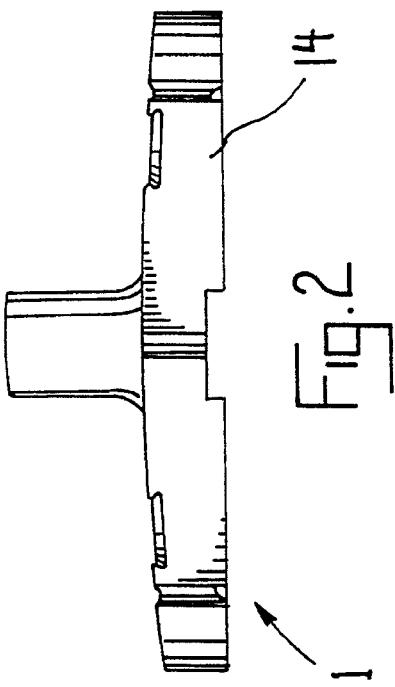
FIG. 3 is a front view of the component of FIG. 1 showing a representative example of a visible deformity which would occur upon resterilization of the component by exposure to a heated environment.

In a preferred embodiment, the provisional instrument component 1 of the present invention, will be made, at least in part, of a material 14 which can be initially commercially sterilized by gamma irradiation, but which will visibly deform upon resterilization by exposure to a heated environment, thereby preventing reuse of the component. Such visible deformation will change the configuration of the component dimensionally, possibly grossly. FIG. 3 shows a representative example of such visible deformation.

Figure 4:
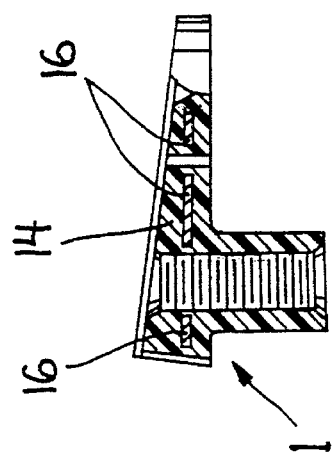
FIG. 4 is a cross-sectional view taken along lines 4—4 of FIG. 1.
Figure 5:
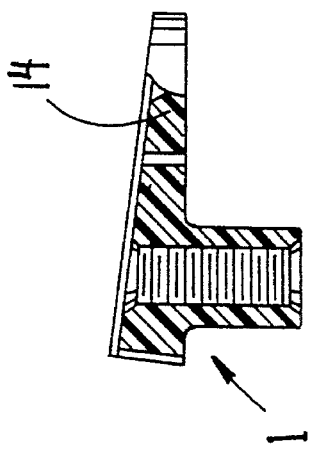
FIG. 5 is a cross-sectional view of an alternate embodiment taken along lines 4—4 of FIG. 1.

The component 1 may be made entirely of such deformable material 14, as shown in FIG. 4, or the component 1 may include a reinforcement portion 16, as shown in FIG. 5. The reinforcement portion is to add strength and stability to component 1 for situations where a stronger provisional component 1 is needed to evaluate the fit of an implant. The reinforcement portion 16 may be made of any suitable material including metal or other appropriate materials, such as those mentioned in the Background of the Invention as suitable reusable materials. The reinforcement portion is preferably not intended to soften or melt at as low of a temperature as the deformable material 14, and thus has a higher melting point than the deformable material 14.

The deformable material 14 is preferably comprised of an acrylic material which is designed to soften or melt, or otherwise visibly deform, when exposed to the heated environment, such as in a steam sterilizer. Preferably the acrylic material includes poly methyl methacrylate (PMMA), either reactor polymerized PMMA or PMMA molded from a liquid molding compound containing a combination of PMMA and methyl methacrylate (MMA). This preferred PMMA liquid molding compound also includes benzoyl peroxide and N,N-dimethyl-P-Toluidine. This acrylic material may further include methyl acrylate (MA) to control thermal properties of the component. Other suitable acrylic resins may be utilized for the deformable material 14, which would visibly deform upon exposure to a heated environment, such as in a steam sterilizer.

Figure 6:
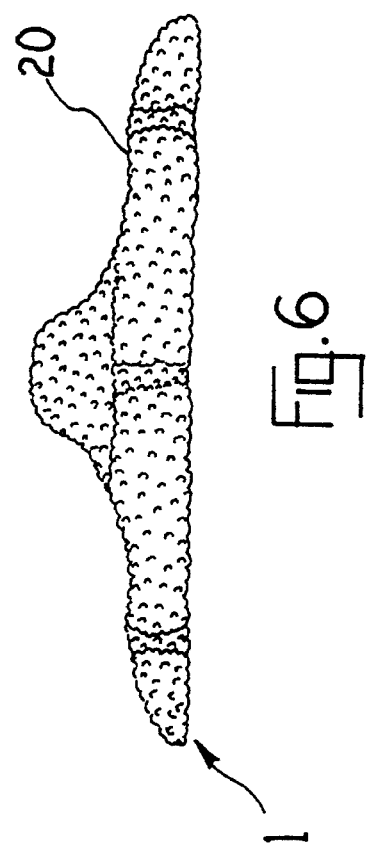
FIG. 6 is a front view of the component of FIG. 1 showing an alternate example of a visible deformity which could occur upon resterilization of the component by exposure to a heated environment.

It is noted that the deformable material 14 could also include a mineral in an effective amount which when heated, such as by steam sterilization, will release gas and cause visible deformation in the form of small bumps and/or bubbles 20 on the component 1, such as in FIG. 6. The mineral may be porous particles of sodium aluminosilicate and potassium aluminosilicate. For example, a suitable acrylic material, preferably PMMA molded from a liquid molding compound, may contain 15 percent porous sodium/ potassium aluminosilicate beads. Such formulation has been tested and shown to cause visible bumps or bubbles 20 when subjected to steam sterilization in an autoclave at 270° F., 27 psi for 15 minutes. The amount of mineral used in the material 14 will typically affect the amount of bumps or bubbles on the surface of component 1. This transformation of the mineral-containing material 14 evidenced by the bumps and/or bubbling 20 on the surface of the component 1 caused by heat sterilization provides a visible indicator that the provisional instrument component should be disposed of and not reused.

The disposable provisional component 1 may be manufactured by any suitable manufacturing technique, including injection molding, extrusion, machining, or casting. Preferably resin transfer molding (RTM) may be used when the deformable material 14 is an acrylic liquid molding compound. However, any suitable manufacturing method may be used.

Molding of the deformable material 14 allows the disposable acrylic provisional component to be made of any suitable desirable shape according to the corresponding mold, and allows the whole provisional component to be made of the acrylic material, if desired. Alternatively, the deformable material 14 may be molded about the reinforcement portion 16 or otherwise suitably applied to reinforcement portion 16, when such a reinforcement portion 16 is provided. The reinforcement portion 16 may be manufactured by any suitable manufacturing technique. Suitable filler, such as barium sulfate, or fiber reinforcements, such as glass fiber, carbon fiber, acrylic fiber, or UHMWPE fiber, may be incorporated into the deformable material 14, if desired.

Provisional components made from the PMMA or PMMA/MMA formulation are also characterized by a low glass transition temperature and deformability when subjected to a heated environment, such as the about 250° F. to 270° F. or greater temperatures associated with steam sterilization or autoclaving. Such acrylic components are initially sterilizable by the commercially available process of gamma irradiation. By designing the disposable provisional component to deform upon resterilization by exposure to a heated environment, such as a steam sterilizer, this prevents the surgeon from reusing this disposable provisional component by providing a distinct visible indication or indicator that the provisional component (due to its deformation upon steam resterilization) is not suitable for reuse. By not being able to resterilize and reuse the disposable provisional component due to such deformation, this ensures the accuracy of the provisional component for testing and evaluating the fit of the corresponding prosthetic implant.

The formulation or particular composition of the deformable material 14, such as an acrylic material, can be optimized as desired by determining the optimum molecular weight, the optimum desired temperature at which the cured acrylic material will deform, as well as by controlling other features or handling characteristics of the acrylic material. Such optimization of handling characteristics can be carried out by someone skilled in chemistry or in the field of materials, such as acrylics, or the like. It is noted that acrylic compositions utilizing PMMA formulations have been used for surgical bone cements (grouting material) or used to precoat a base prosthetic implant, such as a base metallic hip or knee implant.

In addition, other suitable materials which would visibly deform in a heated environment, such as in a steam sterilizer, may be used for the deformable material 14, including a polymer such as poly caprolactone. This polymer melts at 212° F. (100° C.) and hence would modify the surface of the deformable material 14 upon exposure to steam sterilization. In addition, this material would also stick to any packing material or container during the heat sterilization step, and hence disfigure the part.

The provisional instrument component 1 may provide other visible indicators (rather than or in addition to physical deformation) upon resterilization by exposure to a heated environment to help prevent reuse of the component, including, but not limited to the following. The component 1 may include a heat sensitive coloring agent or temperature indicator strips which would change color upon exposure to a heated environment. For example, the coloring agent or temperature indicator strips could be selectively applied to an outer surface or just below the surface of the component 1, so that a word such as "DISCARD" (not shown in the Figs.) would become visible upon exposure to the heated environment. Such heat sensitive coloring agents and temperature indicator strips are known for other uses and, as such, will not be specifically described herein.

While this invention has been described in terms of a particularly advantageous embodiment, those skilled in the art can appreciate that modifications can be made without departing from the spirit and scope of this invention.

We claim:

1. A provisional instrument component for evaluating the fit of a corresponding orthopaedic implant, wherein the component is intended and designed to be a disposable, single use provisional surgical instrument component, and wherein the provisional instrument component is comprised of a material which can be sterilized by gamma irradiation, but which provides a visible indicator upon resterilization by exposure to a heated environment to discourage or prevent reuse of the component, and wherein the provisional component includes performance characteristics which are not suitable or strong enough for implant use in a static or dynamic loaded environment, but which are suitable for provisional use for evaluating the fit of the corresponding implant.

2. The component of claim 1 wherein the visible indicator is visible deformation of the component upon resterilization by exposure to a heated environment.

3. The component of claim 2 wherein the component is comprised of a material which will visibly deform upon exposure to temperatures of about 250° F. or greater.

4. The component of claim 2 wherein the component is comprised of a material which will visibly deform upon exposure to the heated environment of steam sterilization.

5. The component of claim 2 wherein the component is comprised of an acrylic material which is designed to soften or melt, or otherwise visibly deform, when exposed to the heated environment.

6. The component of claim 5 wherein the acrylic material is comprised of poly methyl methacrylate.

7. The component of claim 5 wherein the acrylic material is comprised of a combination of poly methyl methacrylate and methyl methacrylate.

8. The component of claim 5 wherein the acrylic material is a liquid molding compound including poly methyl methacrylate, methyl methacrylate, benzoyl peroxide and N,N-Dimethyl-P-Toluidine.

9. The component of claim 5 wherein the acrylic material further includes a fiber reinforcement or filler.

10. The component of claim 1 wherein the component further includes a reinforcement portion.

11. The component of claim 1 wherein the material includes a temperature sensitive color indicator which will change color upon exposure to the heated environment.

12. A provisional instrument component for evaluating the fit of a corresponding orthopaedic implant, wherein the component is intended and designed to be a disposable, single use provisional surgical instrument component, and wherein the provisional instrument component is comprised of a material which can be sterilized by gamma irradiation, but which provides a visible indicator upon resterilization by exposure to a heated environment to discourage or prevent reuse of the component, and wherein the material includes a mineral which will release gas and cause visible deformation in the form of bumps or bubbles on the component upon exposure to the heated environment.

13. A provisional instrument component for evaluating the fit of a corresponding orthopaedic implant, wherein the component is intended and designed to be a disposable, single use provisional surgical instrument component, and wherein the provisional instrument component is comprised of a material which provides a visible indicator upon resterilization by exposure to a heated environment to discourage or prevent reuse of the component, and wherein the material includes a mineral which will release gas and cause visible deformation in the form of bumps or bubbles on the component upon exposure to the heated environment.

14. A provisional instrument component for evaluating the fit of a corresponding orthopaedic implant, wherein the component is intended and designed to be a disposable, single use provisional surgical instrument component, and wherein the provisional instrument component is comprised of a material which can be initially sterilized in a nonheated environment, but which provides a visible indicator upon resterilization by exposure to a heated environment to discourage or prevent reuse of the component, and wherein the provisional component includes performance characteristics which are not suitable or strong enough for implant use in a static or dynamic loaded environment, but which are suitable for provisional use for evaluating the fit of the corresponding implant.

* * * * *

UNITED STATES PATENT AND TRADEMARK OFFICE
CERTIFICATE OF CORRECTION

PATENT NO. : 5,522,897
DATED : June 4, 1996
INVENTOR(S) : King et al.

It is certified that error appears in the above-indentified patent and that said Letters Patent is hereby corrected as shown below:

ON THE COVER PAGE:

In the Related U.S. Application Data Section [62], please delete the date "Apr. 20, 1994" and substitute therefor --Apr. 26, 1994--

In column 1, line 6, please delete the date "April 20, 1994" and substitute therefore -- April 26, 1994--.

Signed and Sealed this

First Day of October, 1996

Attest:

BRUCE LEHMAN

Attesting Officer   Commissioner of Patents and Trademarks